US007727959B2

(12) United States Patent
Uvnäs-Moberg et al.

(10) Patent No.: US 7,727,959 B2
(45) Date of Patent: Jun. 1, 2010

(54) USE OF SUBSTANCES WITH OXYTOCIN ACTIVITY AGAINST CLIMACTERIC DISORDERS

(75) Inventors: Kerstin Uvnäs-Moberg, Djursholm (SE); Thomas Lundeberg, Lidingö (SE)

(73) Assignee: Pep-Tonic Medical AB, Vaxjo (SE)

( * ) Notice: Subject to any disclaimer, the term of this patent is extended or adjusted under 35 U.S.C. 154(b) by 0 days.

(21) Appl. No.: 11/345,218

(22) Filed: Feb. 2, 2006

(65) Prior Publication Data

US 2006/0148685 A1    Jul. 6, 2006

Related U.S. Application Data

(62) Division of application No. 10/258,013, filed as application No. PCT/SE01/00854 on Apr. 18, 2001, now abandoned.

(30) Foreign Application Priority Data

Apr. 18, 2000    (SE)    .................................... 0001440

(51) Int. Cl.
*A61K 38/11*    (2006.01)
(52) U.S. Cl. ...................................................... 514/15
(58) Field of Classification Search ...................... None
See application file for complete search history.

(56) References Cited

U.S. PATENT DOCUMENTS

| 4,889,844 | A | * | 12/1989 | Silvetti et al. ............ 424/78.25 |
| 5,457,128 | A | * | 10/1995 | Yanagawa .................. 514/532 |
| 5,753,266 | A | * | 5/1998 | Youssefyeh et al. ......... 424/484 |
| 6,260,621 | B1 | * | 7/2001 | Furman et al. ........... 166/280.1 |
| 6,333,313 | B1 | * | 12/2001 | Copland et al. ................ 514/12 |
| 2004/0176284 | A1 | | 9/2004 | Uvnas-Moberg et al. | |

FOREIGN PATENT DOCUMENTS

| WO | WO 9843661 A1 | * | 10/1998 |
| WO |     00/18424 |   |  4/2000 |
| WO | WO 02/067974 |   |  9/2002 |

OTHER PUBLICATIONS

John A. Copland et al., "Functional Oxytocin Receptors Discovered in Human Osteoblasts," Endocrinology, 1999, pp. 4371-4374.
'Oxytocin' http://www.nlm.nih.gov/medlineplus/druginfo/uspdi/202434.html accessed Oct. 28, 2004. Revised Jun. 30, 1994.
BF Mitchel et al. Reviews of Reproduction (1998)3, 113-122.

* cited by examiner

*Primary Examiner*—Andrew D Kosar
(74) *Attorney, Agent, or Firm*—Young & Thompson

(57) ABSTRACT

The present invention relates to the use of substances with oxytocin activity against climacteric disorders or similar symptoms due to dysfunction in the ovaries. It also relates to a pharmaceutical composition comprising at least one substance with oxytocin activity against climacteric disorders.

27 Claims, 4 Drawing Sheets

USE OF SUBSTANCES WITH OXYTOCIN ACTIVITY AGAINST CLIMACTERIC DISORDERS

This application is a division of co-pending application Ser. No. 10/258,013, filed on Jun. 10, 2003. Application Ser. No. 10/258,013 is the national phase of PCT International Application No. PCT/SE01/00854 filed on Apr. 18, 2001 under 35 U.S.C. § 371, which claims priority of Swedish Application No. 0001440-7 filed Apr. 18, 2000. The entire contents of each of the above-identified applications are hereby incorporated by reference.

The present invention relates to the use of substances with oxytocin activity against climacteric disorders or similar symptoms due to dysfunction in the ovaries. It also relates to a pharmaceutical composition comprising at least one substance with oxytocin activity against climacteric disorders.

BACKGROUND OF THE INVENTION

Oxytocin was one of the first peptide hormones to be isolated and sequenced. It is a nonapeptide with two cysteine residues that form a disulfide bridge between positions 1 and 6 and corresponds to the formula

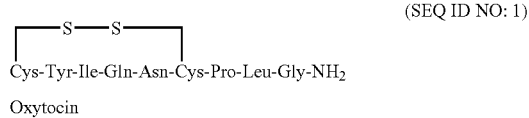

(SEQ ID NO: 1)

Cys-Tyr-Ile-Gln-Asn-Cys-Pro-Leu-Gly-NH$_2$

Oxytocin

For a long time the only effects attributed to oxytocin were its stimulating effects on milk ejection and uterine contractions, but in the past decades it has been shown that oxytocin exerts a wide spectrum of effects within the central nervous system, CNS. It has been suggested that oxytocin participates in the control of memory and learning processes and of various types of behaviour such as feeding, locomotion, as well as maternal and sexual behaviour. Oxytocin is also suggested to participate in the control of cardiovascular functions, thermoregulation, and pain threshold and fluid balance. There is also evidence that oxytocin is involved in the control of various immunological processes. It has recently been demonstrated that oxytocin injections cause a lowering of blood pressure and increased weight gain—long lasting effects after repetitive administration. As a central stimulating substance oxytocin plays an important role in the interaction between mother and progeny in mammals. The products may also be used prophylactic in young human beings e.g. already in new born babies or young children to prevent the development of diseases later on in life which diseases are dependent on stress conditions during the fetal life. Such conditions may be heart/vessel diseases such as stroke, heart infarct, hypertension, and diabetes.

In the human body oxytocin is produced in the paraventricular nucleus, PVN, and the supraoptic nucleus, SON, of the hypothalamus. It differs by only two amino acids from vasopressin, which is also produced in these nuclei. The magnocellular oxytocinergic neurones of the SON and PVN send oxons to the posterior pituitary from which oxytocin is released into the circulation. Parvocellular neurones that originate in the PVN project into multiple areas within CNS. The oxytocin-producing cells are innervated by cholinergic, catecholaminergic as well as peptidergic neurones. The presence of oxytocin in different tissues outside the brain, such as the uterus, ovaries, testis, thymus, adrenal medulla and pancreas has been demonstrated and oxytocin is suggested to exert local effects in these organs.

A parallel secretion of oxytocin into the brain regions and into the circulation occurs in response to some stimuli such as suckling, but other stimuli can cause separate activation of oxytocinergic neurones, terminating in the brain or the pituitary.

It has now turned out that oxytocin has a relieving effect on climacteric disorders.

There are several oxytocin derivatives, i.e. compounds with a structure similar to that of oxytocin. The inventors have preliminary indications that other oxytocin derivatives than oxytocin could give the effects against climacteric disorders and disorders of ovarian functions as well as parts of the oxytocin molecule. No publications describe the use of oxytocin or any other oxytocin derivatives or parts of the oxytocin molecule to have effects against climacteric disorders or other types of premature ovarian dysfunction.

By the expression "climacteric disorders" we understand premenopausal (i e before the menopause), perimenopausal (i e during the menopause) and postmenopausal (i e after the menopause) weight changes, mood swings, hot flushes (transient redness and a feeling of being warm), somatic discomfort, dry and ulcerous mucous membranes, fissures, and bone loss. Such symptoms often occur at the time of the menopause, i e the cessation of menstruation in the human female, occurring usually around the age of 50.

It has now turned out that oxytocin improves the vaginal mucosal membranes of women with postmenopausal disorders and improves the mood of such women (Example 1). In an animal model of menopause, i.e. ovariectomy, oxytocin normalises hormone levels and moderates weight changes (Example 2), increases motor activity and relieves somatic discomfort (Example 3), reduces hot flushes (Example 4), reduces hyperactivity in the sympathetic nervous system (Example 5), and suppresses bone loss (Example 6). These Examples indicate that oxytocin or that substances with oxytocin activity may be used against climacteric disorders and ovarian dysfunction. The oxytocin derivatives according to the invention are not only suitable against postmenopausal disorders but also against premenopausal, perimenopausal and ovarian dysfunction.

The effect of oxytocin can be extended or strengthened by administration in combination with drugs increasing the release of oxytocin and/or the number or affinity of receptors, such as oestrogen, or drugs having an $\alpha_2$-agonistic effect, such as clonidine.

SUMMARY OF THE INVENTION

The present invention relates to the use of substances with oxytocin activity against climacteric disorders. The invention also relates to a pharmaceutical composition comprising an effective concentration of at least one substance with oxytocin activity in mixture or otherwise together with at least one pharmaceutically acceptable carrier or excipient. Such a pharmaceutical composition could be used in order to improve the effects against climacteric disorders.

DETAILED DESCRIPTION OF THE INVENTION

One object of the present invention is the use of a substance with oxytocin activity for the preparation of a pharmaceutical composition against climacteric disorders, such as weight changes, mood swings, hot flushes, dry and ulcerous mucous membranes, fissures, and bone loss.

It is preferred that the substance is selected from the group consisting of the following compounds:

(SEQ ID NO: 2)

wherein $X_1$ is selected from the group consisting of Cys and nothing, $X_2$ is selected from the group consisting of Tyr, Phe, and nothing, $X_3$ is selected from the group consisting of Ile, Val, Hoph, Phe, Cha, and nothing, $X_4$ is selected from the group consisting of Gln, Ser, Thr, Cit, Arg, and Daba, $X_5$ is selected from the group consisting of Pro, and nothing, $X_6$ is selected from the group consisting of Ile, Leu, nothing, Val, Hos, Daba, Thr, and Cit, $X_7$ is selected from the group consisting of Gly, nothing, and Ala, R is a chemical bond or, in the case neither of $X_1$, $X_2$, $X_3$ and $X_4$ represents Cys, represents nothing.

The cystein disulfide bridge in SEQ ID NO: 2 is only present when $X_1$ represents Cys, $X_2$ represents Tyr or Phe, and $X_3$ represents Ile, Val, Hoph, Phe or Cha.

It is even more preferred that the substance is selected from the group consisting of the following compounds:

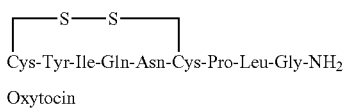
(SEQ ID NO: 1)

Oxytocin $X_1$ is Cys, $X_2$ is Tyr, $X_3$ is Ile, $X_4$ is Gln, $X_5$ is Pro, $X_6$ is Leu, and $X_7$ is Gly in Claim 2 and 7

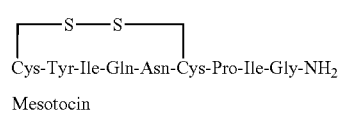
(SEQ ID NO: 3)

Mesotocin $X_1$ is Cys, $X_2$ is Tyr, $X_3$ is Ile, $X_4$ is Gln, $X_5$ is Pro, $X_6$ is Ile, and $X_7$ is Gly in Claim 2 and 7

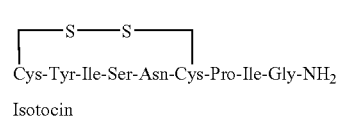
(SEQ ID NO: 4)

Isotocin $X_1$ is Cys, $X_2$ is Tyr, $X_3$ is Ile, $X_4$ is Ser, $X_5$ is Pro, $X_6$ is Ile, and $X_7$ is Gly in Claim 2 and 7

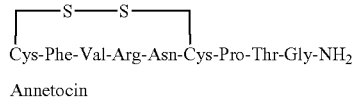
(SEQ ID NO: 5)

Annetocin $X_1$ is Cys, $X_2$ is Phe, $X_3$ is Val, $X_4$ is Arg, $X_5$ is Pro, $X_6$ is Thr, and $X_7$ is Gly in Claim 2 and 7

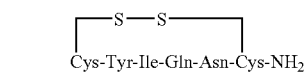
SEQ ID NO: 6

$X_1$ is Cys, $X_2$ is Tyr, $X_3$ is Ile, $X_4$ is Gln, and $X_5$-$X_7$ is nothing in Claim 2 and 7

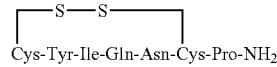
SEQ ID NO: 7

$X_1$ is Cys, $X_2$ is Tyr, $X_3$ is Ile, $X_4$ is Gln, $X_5$ is Pro, and $X_6$-$X_7$ is nothing in Claim 2 and 7

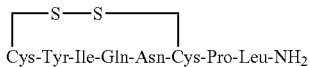
SEQ ID NO: 8

$X_1$ is Cys, $X_2$ is Tyr, $X_3$ is Ile, $X_4$ is Gln, $X_5$ is Pro, $X_6$ is Leu, and $X_7$ is nothing in Claim 2 and 7

```
Tyr-Ile-Gln-Asn-Cys-Pro-Leu-Gly-NH2    SEQ ID NO:9
```

$X_1$ is nothing, $X_2$ is Tyr, $X_3$ is Ile, $X_4$ is Gln, $X_5$ is Pro, $X_6$ is Leu, and $X_7$ is Gly in Claim 2 and 7

```
Ile-Gln-Asn-Cys-Pro-Leu-Gly-NH2    SEQ ID NO:10
```

$X_1$-$X_2$ is nothing, $X_3$ is Ile, $X_4$ is Gln, $X_5$ is Pro, $X_6$ is Leu, and $X_7$ is Gly in Claim 2 and 7

```
Gln-Asn-Cys-Pro-Leu-Gly-NH2    SEQ ID NO:11
```

$X_1$-$X_3$ is nothing, $X_4$ is Gln, $X_5$ is Pro, $X_6$ is Leu, and $X_7$ is Gly in Claim 2 and 7

```
Ile-Gln-Asn-Cys-Pro-NH2    SEQ ID NO:12
```

$X_1$-$X_2$ is nothing, $X_3$ is Ile, $X_4$ is Gln, $X_5$ is Pro, and $X_6$-$X_7$ is nothing in Claim 2 and 7

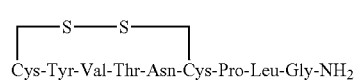
SEQ ID NO: 13

$X_1$ is Cys, $X_2$ is Tyr, $X_3$ is Val, $X_4$ is Thr, $X_5$ is Pro, $X_6$ is Leu, and $X_7$ is Gly in Claim 2 and 7

Cys-Tyr-Hoph-Thr-Asn-Cys-Pro-Val-Gly-NH₂     SEQ ID NO: 14

X₁ is Cys, X₂ is Tyr, X₃ is Hoph, X₄ is Thr, X₅ is Pro, X₆ is Val, and X₇ is Gly in Claim 2 and 7

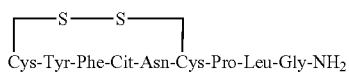
Cys-Tyr-Phe-Cit-Asn-Cys-Pro-Leu-Gly-NH₂     SEQ ID NO: 15

X₁ is Cys, X₂ is Tyr, X₃ is Phe, X₄ is Cit, X₅ is Pro, X₆ is Leu, and X₇ is Gly in Claim 2 and 7

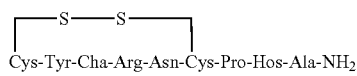
Cys-Tyr-Cha-Arg-Asn-Cys-Pro-Hos-Ala-NH₂     SEQ ID NO: 16

X₁ is Cys, X₂ is Tyr, X₃ is Cha, X₄ is Arg, X₅ is Pro, X₆ is Hos, and X₇ is Ala in Claim 2 and 7

Cys-Tyr-Val-Daba-Asn-Cys-Pro-Daba-Ala-NH₂     SEQ ID NO: 17

X₁ is Cys, X₂ is Tyr, X₃ is Val, X₄ is Daba, X₅ is Pro, X₆ is Daba, and X₇ is Ala in Claim 2 and 7

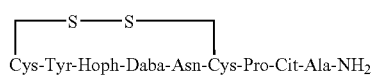
Cys-Tyr-Hoph-Daba-Asn-Cys-Pro-Cit-Ala-NH₂     SEQ ID NO: 18

X₁ is Cys, X₂ is Tyr, X₃ is Hoph, X₄ is Daba, X₅ is Pro, X₆ is Cit, and X₇ is Ala in Claim 2 and 7

Cys-Tyr-Phe-Arg-Asn-Cys-Pro-Val-Ala-NH₂     SEQ ID NO: 19

X₁ is Cys, X₂ is Tyr, X₃ is Phe, X₄ is Arg, X₅ is Pro, X₆ is Val, and X₇ is Ala in Claim 2 and 7,
wherein Cha stands for cyclohexylalanine,

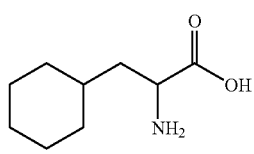

Hoph stands for homophenylalanine,

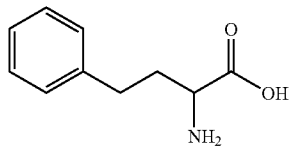

Cit stands for citruline,

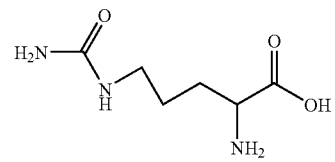

Daba stands for diaminobutyric acid, and

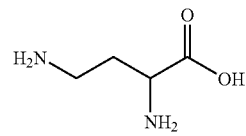

Hos stands for homoserine.

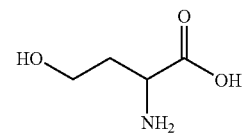

There are different processes described for the synthetical production of oxytocin; commercial processes are for instance described in U.S. Pat. Nos. 2,938,891 and 3,076,797.

A substance with oxytocin activity refers, whenever applicable, in addition to oxytocin also to precursors, metabolic derivatives, oxytocin agonists or analogues displaying the same properties. It can be shown that a substance has oxytocin activity by performing tests showing the activity of the actual substance e g by performing a double blind cross-over randomised protocol as described in Example 1.

Annetocin has been isolated from the earthworm, as described in Oumi T, Ukena K, Matsushima O, Ikeda T, Fujita T, Minakata H, Nomoto K, Annetocin: an oxytocin-related peptide isolated from the earthworm, *Eisenia foetida*, *Biochem Biophys Res Commun* 1994, Jan. 14; 198(1): 393-399.

Other substances with oxytocin activity could also be used, such as naturally occurring or artificially modified variants, analogues, and derivatives of oxytocin, mesotocin, isotocin, and annetocin. Such substances could be obtained by addition, insertion, elimination, or substitution of at least one amino acid in these hormones. By a substance with an oxytocin like activity is also understood precursors, metabolites such as metabolic derivatives e.g. metabolic degradation products, agonists, or analogues of the substances mentioned herein displaying the same properties. Metabolic derivatives or metabolic degradation products may be oxytocin like peptides e.g. with nine amino acids such as oxytocin, mesotocin, isotocin, and annetocin from which one or more amino acids has been deleted from either the carboxyl terminal end or the amino terminal end or both the carboxyl terminal and the amino terminal end, preferably 1-3 amino acids from each terminal. It could be ascertained that these variants are analogues of oxytocin, mesotocin, isotocin or annetocin by immunological methods, e.g. RIA (radioimmunoassay), IRMA (radiometric methods), RIST (radioimmunosorbent test), and RAST (radioallergosorbent test). The invention also includes substances having at least 50, 60, 70, 80 and most preferably 90% homology to oxytocin, and showing oxytocin activity.

As mentioned above there are indications that subfragments of the oxytocin molecule could have effects against climacteric disorders. Examples of subfragments of the oxytocin molecule are the following compounds: SEQ ID NO: 6, SEQ ID NO: 7, SEQ ID NO: 8, SEQ ID NO: 9, SEQ ID NO: 10, SEQ ID NO: 11, and SEQ ID NO: 12.

There is also a possibility to create new compounds with oxytocin activity by means of computer simulation. Methods for computer simulation are known by a person skilled in the art, e.g. as described in EP 0660 210 A2. Seven new compounds have been created by means of computer simulation, namely the following peptides: SEQ ID NO: 13, SEQ ID NO: 14, SEQ ID NO: 15, SEQ ID NO: 16, SEQ ID NO: 17, SEQ ID NO: 18, and SEQ ID NO: 19.

The invention also relates to the peptides mentioned above in both D- and L-form, and racemates thereof. Especially the invention relates to the L-form. By inversion of the peptide sequence thereof, the D-form could be converted to the L-form. The effect of the D- and L-forms are the same. These and the peptides above can be produced by methods known to a person skilled in the art, e.g. according to Merrifield, P. B., "Solid Phase Synthesis", *Angew. Chemie,* 1985, No. 97, p. 801.

The pharmaceutical compositions according to the invention may contain substances that extend or strengthen the effects of oxytocin. Such substances could increase the release of oxytocin and/or the number or affinity of oxytocin receptors, such as oestrogen, or drugs having an $\alpha_2$-agonistic effect, such as clonidine.

It is preferred that a substance with oxytocin activity is administered in an amount of 0.01-100 ng/kg body weight of the patient, in particular 0.1-10 ng/kg.

Another object of the invention is a pharmaceutical composition against climacteric disorders comprising an effective concentration of at least one substance with oxytocin activity in mixture or otherwise together with at least one pharmaceutically acceptable carrier or excipient. It is preferred that the substance is selected from the group consisting of compounds with the formula SEQ ID NO: 2. It is even more preferred that the substance is selected from the group consisting of the following compounds: SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19.

The pharmaceutical compositions according to the invention may contain substances that extend or strengthen the effects of oxytocin. Such substances could increase the release of oxytocin and/or the number or affinity of oxytocin receptors, such as oestrogen, or drugs having an $\alpha_2$-agonistic effect, such as clonidine.

The pharmaceutical compositions are prepared in a manner known to a person skilled in the pharmaceutical art. The carrier or the excipient could be a solid, semi-solid or liquid material that could serve as a vehicle or medium for the active ingredient. Suitable carriers or excipients are known in the art. The pharmaceutical composition could be adapted to oral, parenteral, intravaginal, or topical use and could be administered to the patient as tablets, capsules, suppositories, solutions, suspensions or the like.

The pharmaceutical compositions could be administered orally, e.g. with an inert diluent or with an edible carrier. They could be enclosed in gelatine capsules or be compressed to tablets. For oral therapeutic administration the compounds according to the invention could be incorporated with excipients and used as tablets, lozenges, capsules, elixirs, suspensions, syrups, wafers, chewing gums and the like. These preparations should contain at least 4% by weight of the compounds according to the invention, the active ingredient, but could be varied according to the special form and could, suitably, be 4-70% by weight of the unit. The amount of the active ingredient that is contained in compositions is so high that a unit dosage form suitable for administration is obtained.

The tablets, pills, capsules, lozenges and the like could also contain at least one of the following adjuvants: binders such as microcrystalline cellulose, gum tragacanth or gelatine, excipients such as starch or lactose, disintegrating agents such as alginic acid, Primogel, corn starch, and the like, lubricants such as magnesium stearate or Sterotex, glidants such as colloidal silica dioxide, and sweetening agents such as saccharose or saccharin could be added or flavourings such as peppermint, methyl salicylate or orange flavouring. When the unit dosage form is a capsule it could contain in addition to the type above a liquid carrier such as polyethylene glycol or a fatty oil. Other unit dosage forms could contain other different materials that modify the physical form of the unit dosage form, e.g. as coatings. Accordingly, tablets or pills could be coated with sugar, shellac or other enteric coating agents. A syrup could in addition to the active ingredient contain saccharose as a sweetening agent and some preservatives, dyes and flavouring agents. Materials that are used for preparation of these different compositions should be pharmaceutically pure and non-toxic in the amounts used.

For parenteral administration the compounds according to the invention could be incorporated in a solution or suspension. Parenteral administration refers to the administration not through the alimentary canal but rather by injection through some other route, as subcutaneous, intramuscular, intraorbital, intracapsular, intraspinal, intrasternal, intravenous, intranasal, intrapulmonary, through the urinary tract, through eye drops, rectal or intravaginal (e.g. as a suppository, a vagitorium, a cream or an ointment), through the lactiferous tract in cattle, into an organ such as bone marrow, etc. Bone marrow may also be treated in vitro. These preparations could contain at least 0.1% by weight of an active compound according to the invention but could be varied to be approximately 0.1-50% thereof by weight. The amount of the active ingredient that is contained in such compositions is so high that a suitable dosage is obtained.

The solutions or suspensions could also comprise at least one of the following adjuvants: sterile diluents such as water for injection, saline, fixed oils, polyethylene glycols, glycerol, propylene glycol or other synthetic solvents, antibacterial agents such as benzyl alcohol or methyl paraben, antioxidants such as ascorbic acid or sodium bisulfite, chelating agents such as ethylene diamine tetraacetic acid, buffers such as acetates, citrates or phosphates, and agents for adjustment of the tonicity such as sodium chloride or dextrose. The parenteral preparation could be enclosed in ampoules, disposable syringes or multiple dosage vessels made of glass or plastic.

For topical administration the compounds according to the invention could be incorporated in a solution, suspension, ointment, or gel. These preparations could contain at least 0.1% by weight of an active compound according to the invention but could be varied to be approximately 0.1-50% thereof by weight. The amount of the active ingredient that is contained in such compositions is so high that a suitable dosage is obtained. The administration could be facilitated by applying touch, pressure, massage, heat, warms, or infrared light on the skin, which leads to enhanced skin permeability. Hirvonen, J., Kalia, Y N, and Guy, R H. Transdermal delivery of peptides by iontophoresis, *Nat Biotechnol* 1996 December; 14(13): 1710-1713 describes how to enhance the transport of a drug via the skin using the driving force of an applied electric field. Preferably, iontophoresis is effected at a slightly basic pH.

Other administration forms are inhalation through the lungs, buccal administration via the mouth, enteral administration via the small intestine, and local administration with a release, preferably a slow release, of the active substance e g in the form of a ring. All these administration forms could be effected by means known by a person skilled in the art.

All publications mentioned herein are hereby incorporated by reference. By the expression "comprising" we understand including but not limited to. Thus, other non-mentioned substances, additives or carriers may be present.

SHORT DESCRIPTION OF THE FIGURES

FIG. 1 is a bar graph showing the plasma concentration of insulin in ovariectomised rats administered subcutaneously with saline (NaCl) and oxytocin.

FIG. 2 is a bar graph showing the plasma concentrations of corticosterone and growth hormone (GH) in ovariectomised rats subjected to subcutaneous treatment. Group A refers to rats treated with oestrogen, progesterone, and oxytocin. Group B refers to rats treated with oestrogen and progesterone. Group C refers to rats treated with oxytocin. Group D refers to rats treated with saline.

Figure 1:
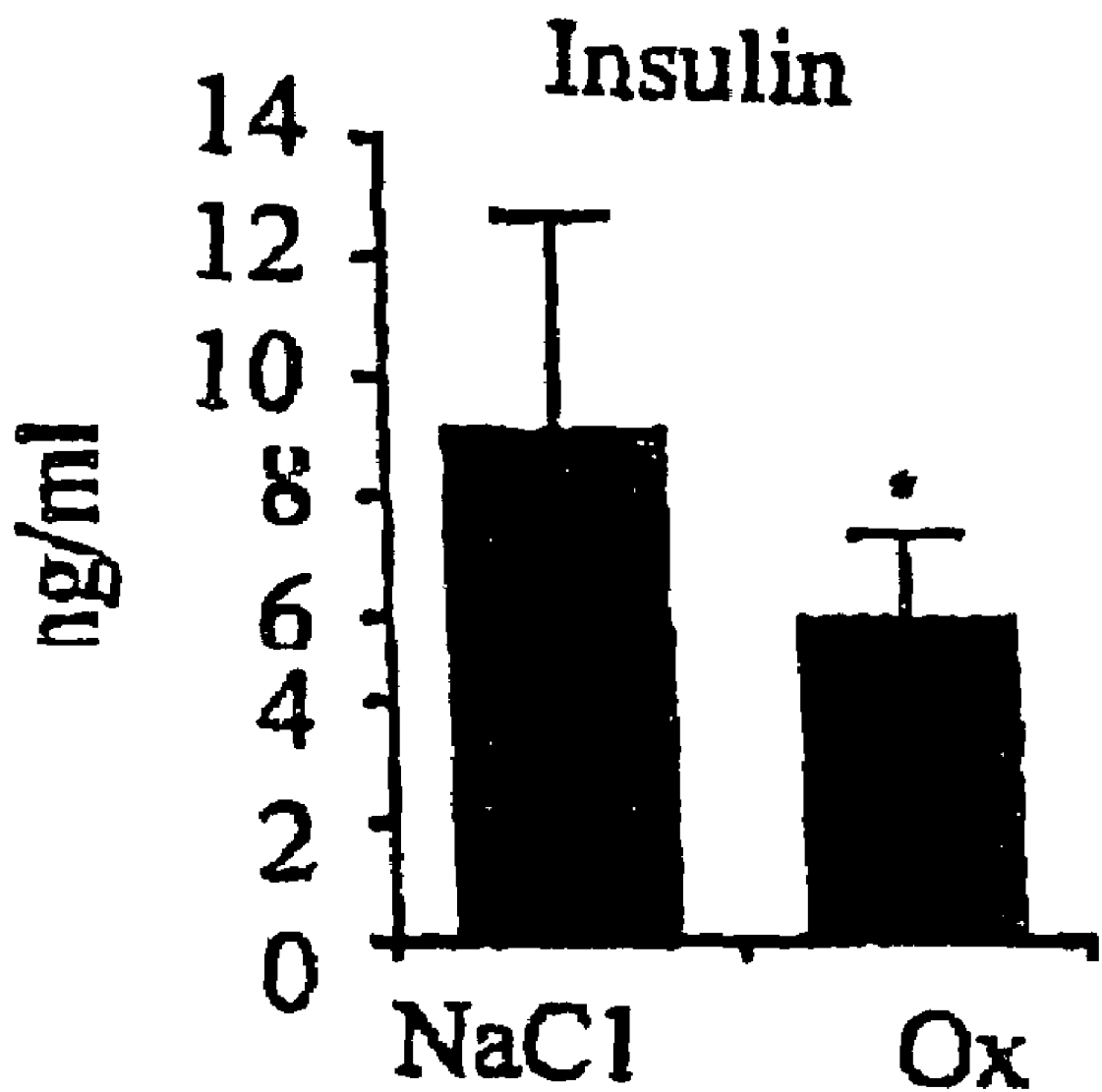

The invention will be illuminated by the following Examples, which are only intended to illuminate and not restrict the invention in any way.

EXAMPLES

Materials and Methods

Animals (Example 2-3)

Female sexually mature Sprague-Dawley rats weighing 250-300 g were used (B&K Universal, Sollentuna, Sweden). The rats were housed 5 to each cage with free access to food and tap water at 20±2° C. and with a 12 h light/12 h dark cycle for at least 3 weeks before and throughout the experimental period.

Animals (Example 4-5)

Virgin adult cycling Sprague-Dawley rats weighing 300-350 g (Example 4) and 190-210 g (Example 5) and with regular 4-day oestrous cycles were used (Möllegaard, Denmark). The rats were housed 4 to each cage with free access to pelleted food and tap water at 22° C. and with a 12 h light/12 h dark cycle for at least 1 week before and throughout the experimental period.

Animals (Example 6)

Four lots of 120-day-old female Wistar rats (mean±SD initial weight 273±28 g) were used. The rats were randomized into groups based on their body weight. Rats weighing the most and those weighing the least were assigned each time alternatively to one group, so at the end of the randomization process the mean body weight of each group was comparable. Sample size was calculated in a pilot study after determining the variability of densitometric measurements.

All rats were fed standard chow feed containing 7.1 g/kg of calcium and 5 g/kg of phosphorus; the energy content of the feed was 3100 kcal/kg. A control group of 15 rats were not manipulated but fed the standard diet (control group, mean initial weight 269±31 g). An experimental group of 15 rats was ovariectomized at 120 days of life and given oxytocin for 10 days 1.0 mg/kg sc. (OVX+Oxy group, mean initial weight 277±32 g). A group of 15 rats underwent ovariectomy (OVX group, mean initial weight 282±27 g). The OVX group did not receive oxytocin and was fed the standard diet. The ovariectomy was performed as in previous studies [Rico H, Amo C, Revilla M, Arribas I, Gonzalez-Riola J, Villa L F, Rodriguez-Puyol M Etidronate versus Clodronate in the prevention of postovariectomy bone loss. An experimental study in rats. *Clin Exp Rheumatol* 1994, 12:301-304]. The manipulated rats were controlled to observe the development of intestinal function, alterations, and infection or dehiscence of surgical sutures. All rats received water ad libitum. The rats were kept for 30 days in the animal laboratory of department of Physiology and Pharmacology, Karolinska Institutet. Living conditions (12 hours of light and 12 hours of darkness; mean room temperature 22° C.), habitat, and diet met current guidelines of the European Union. Weight was measured with a precision biomedical balance.

Ovariectomy

Ovariectomy means removal of an ovary or ovaries and can e g be effected according to Merchentaler, I., Funkhouser, J. M., Carver, J. M., Lundeen, S. G., Ghosh, K., Winneker, R. C. The effect of estrogens and antiestrogens in a rat model for hot flush. *Maturitas,* 1998, Nov. 16; 30(3): 307-316.

Statistics (Example 1-3 and 6)

The results are presented as means±SD. Statistical analysis was performed by means of a one-way ANOVA, followed by Dunnett's t-test for post hoc comparisons. $^{ns}p>0.05$; $*p<0.05$; $**p<0.01$.

Statistics (Example 4-5)

Statistical analyses were carried out using the SPSS 8.0 software. NGF concentrations in the pituitary gland, the hypothalamus, the hippocampus, the ovary, and the adrenal glands were analysed and the groups compared using analyses of variance (ANOVA) followed by multiple comparison procedures (Bonferroni test).

All results are presented as mean±standard error of mean (SEM). A p-value less than 0.05 is considered significant. The 95% confidence interval (CI) was given when $p<0.05$.

Example 1

Intravaginal Oxytocin Administration to Postmenopausal Women

Seven women at an age of 60-70 years, otherwise completely healthy, with expressed postmenopausal disorders in the form of white, thin, atrophic, easy-bleeding and ulcerous vaginal mucous membranes were included in the study. They were treated with oxytocin 1 mg/ml mixed with 1 ml cellulose gel intravaginally during five consecutive days.

The treatment was effected by a gynaecologist who inspected the mucous membranes. After a treatment lasting 2-3 days, the mucous membranes had improved in that they looked like those in a fertile woman. They were all perfused with blood and all ulcers had disappeared.

At the same time, it was observed that the mood of the women was improved. They seemed obviously happy and reported that they felt happy, and many of them had resumed their sex lives.

Atrophic mucous membranes have formerly been treated with oestrogen cream or gel with oestradiol or oestrone as an active substance. Then, a certain improvement is observed after a treatment of approximately 2 weeks, but the improvement is not as complete as after the preliminary observations with the oxytocin gel. Furthermore, the improvement is often preceded by a period with local itch and irritation. No mood improvement has been observed after a local oestrogen treatment.

Besides, a further experiment was conducted, wherein 20 women, all of them at two years into menopause and otherwise healthy. None of them underwent hormone replacement therapy. All patients had objective and subjective symptoms of vaginal rash, pain and a feeling of dryness.

Ten patients were treated with oxytocin 1 mg/ml mixed with 1 ml cellulose gel intravaginally during five consecutive days, whereas the remaining ten patients were treated with 1 ml cellulose gel intravaginally during five consecutive days as control. Before treatment with either control or oxytocin gel we took a biopsy, this procedure was repeated after 5 days of treatment. The protocol was a double blind protocol, i e the microscopic evaluations were performed by the same experienced pathologist before the code was broken.

None of the women receiving control showed improvement in the microscopic evaluation, and they did not express subjective relief in the interviews. The women with oxytocin treatment expressed relief and the histology showed normalization of the epithelium (except in the cases where the mucous epithelium was normal before treatment) and also no or a lesser degree of inflammation.

Example 2

Subcutaneous Oxytocin Administration to Rats

In an experimental animal study, eight ovariectomised rats were treated with oxytocin. The ovaries were removed in order to create a menopause-like situation. After a month, an endocrine study was made. The "menopausal" rats get a changed hormone balance. Their insulin levels and, to a certain extent, their blood sugar levels rise, possibly in consequence of increased insulin resistance. Their cortisol and growth hormone levels decrease, which expresses an inability to mobilise calories for activity. An oxytocin treatment during five days (1 mg/kg given subcutaneously during five days) restored the hormone balance. The insulin levels were normalised i e lowered in oxytocin treated rats compared to control rats treated with NaCl (see FIG. 1), as well as the blood sugar levels.

Figure 2:
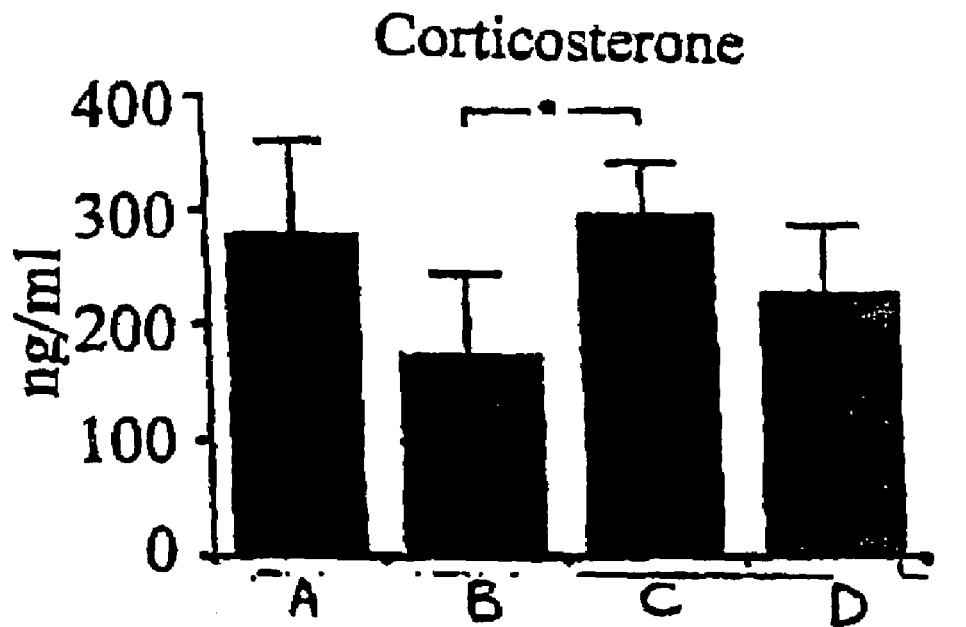
Figure 2:
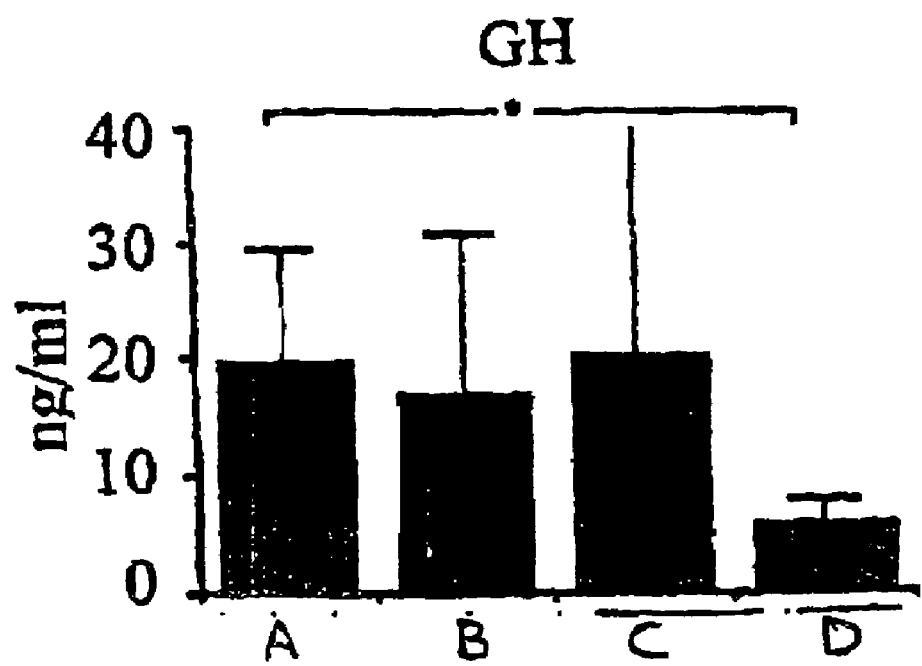

In another experimental animal study, the effect of oxytocin (1 mg/kg given subcutaneously during five days) combined with hormone treatment was investigated. All treatment groups A-D each contained eight ovariectomised rats. The corticosterone levels were significantly higher in rats treated with oxytocin only than in rats treated with oestrogen+progesterone. The GH levels were significantly higher in rats treated with oestrogen+progesterone+oxytocin, oestrogen+progesterone, or oxytocin than in saline treated rats (see FIG. 2). Analogously to the insulin levels, the corticosterone and GH levels were normalised (but increased) by oxytocin treatment.

Figure 3:
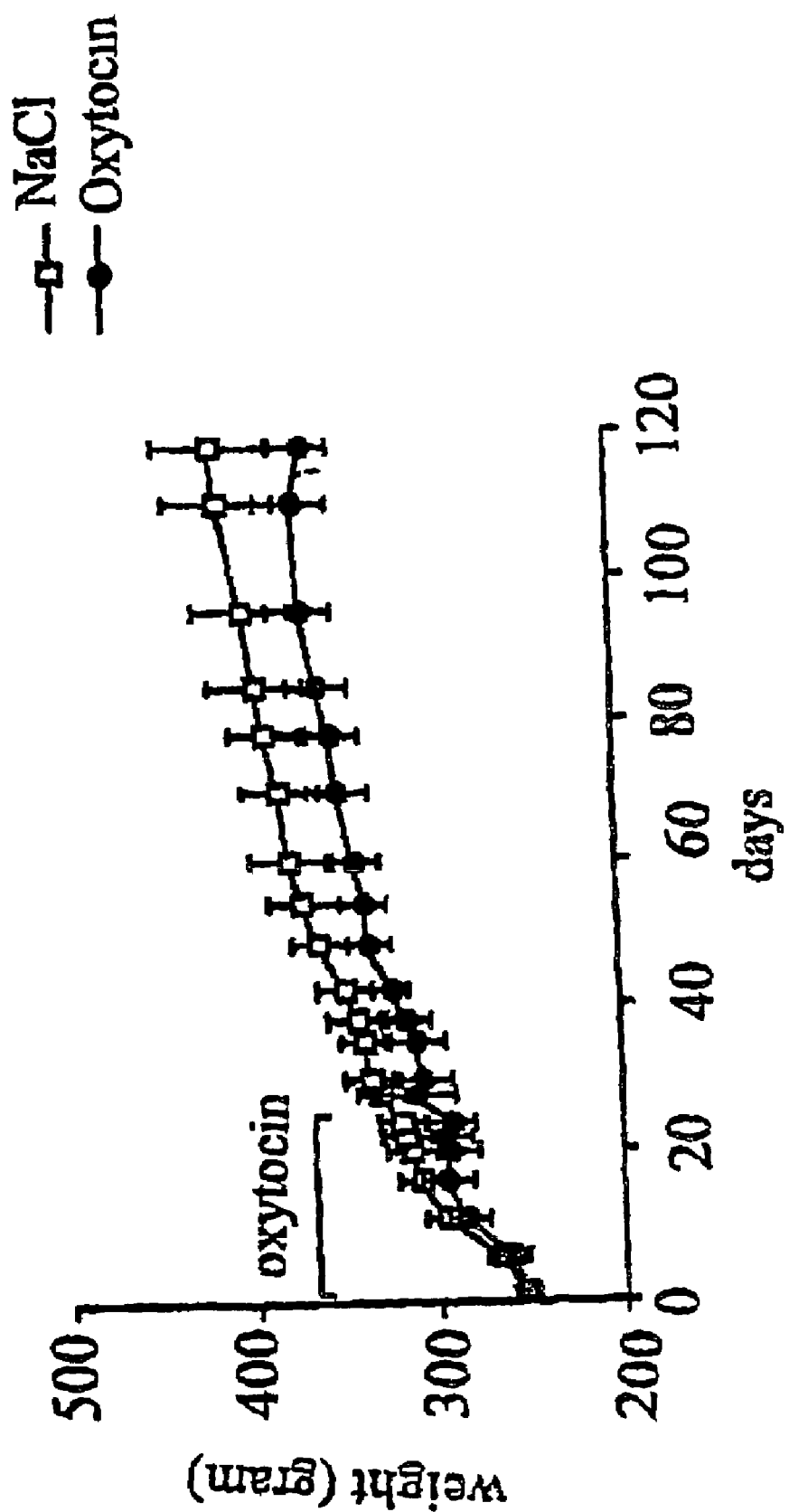
FIG. 3 shows the weight change in ovariectomised rats in response to consecutively given subcutaneous treatments with oxytocin compared to controls receiving saline.

A rat having its ovaries removed also gains weight compared to untreated rats. Rats treated with oxytocin for 10 days do not gain weight as much despite of the fact that they do not eat less (see FIG. 3).

Example 3

Intravaginal Oxytocin Administration to Ovariectomised Rats

The ovaries of seven female rats were removed. After 2 weeks, the rats were treated with oxytocin gel given intravaginally (conc. 1 mg/ml). Two days after completed treatment, the rats given oxytocin showed some behaviour changes reflecting an increased motor activity such as forward locomotion compared to rats only treated with gel without oxytocin. This indicates that it is possible to create central oxytocin effects by giving oxytocin intravaginally, even in rats. Most probably, there is an activation of nerves present in the vaginal mucous membrane.

The following Table I shows the forward locomotion of ovariectomised rats (rats R1-R7) after intravaginal oxytocin administration compared to saline administered control rats (rats B1-B7). By forward locomotion is meant successive interruptions of photocells in the lower rows when the animal is moving in the same direction, i.e. initially, the location of the animal is defined by the photocell being interrupted, the next interruption indicates that the animal is moving, and successive interruptions are registered as locomotion, as long as the animal moves along the same vector (for further details, see Carter, S. Oxytocin and sexual behavior. *Neurosci. Biobehav. Rev.* 16:131-144; 1992). The total experimental time is 30 minutes per rat, and the values in table I show the forward locomotion for the first 15 minutes, for the whole experimental time, and for the last 15 minutes.

TABLE I

|  | Minutes 1-15 | Minutes 16-30 | Minutes 1-30 |
| --- | --- | --- | --- |
| Control |  |  |  |
| B1 | 23.9 | 24.6 | 24.2 |
| B2 | 24.7 | 15.9 | 22.1 |
| B3 | 27.4 | 22.5 | 25.5 |
| B4 | 24.5 | 9.5 | 22.6 |
| B5 | 31.3 | 16.8 | 26.7 |
| B6 | 30.6 | 22.5 | 27.6 |
| B7 | 27.3 | 16.5 | 24.3 |
| AVERAGE | 27.10 | 18.33 | 24.71 |
| SD | 2.97 | 5.22 | 2.03 |
| Oxytocin |  |  |  |
| R1 | 30.7 | 20.3 | 27.7 |
| R2 | 27.8 | 19.8 | 25.3 |
| R3 | 28.8 | 17.7 | 25.1 |
| R4 | 28.6 | 23.2 | 26.3 |
| R5 | 32.2 | 21.6 | 28.7 |
| R6 | 32.3 | 15.3 | 27.7 |
| R7 | 31 | 23 | 27.6 |
| AVERAGE | 30.20 | 20.13 | 26.91 |
| SD | 1.81 | 2.86 | 1.36 |
| T-test | 0.04* | 0.44 ns | 0.03* |

Figure 4:
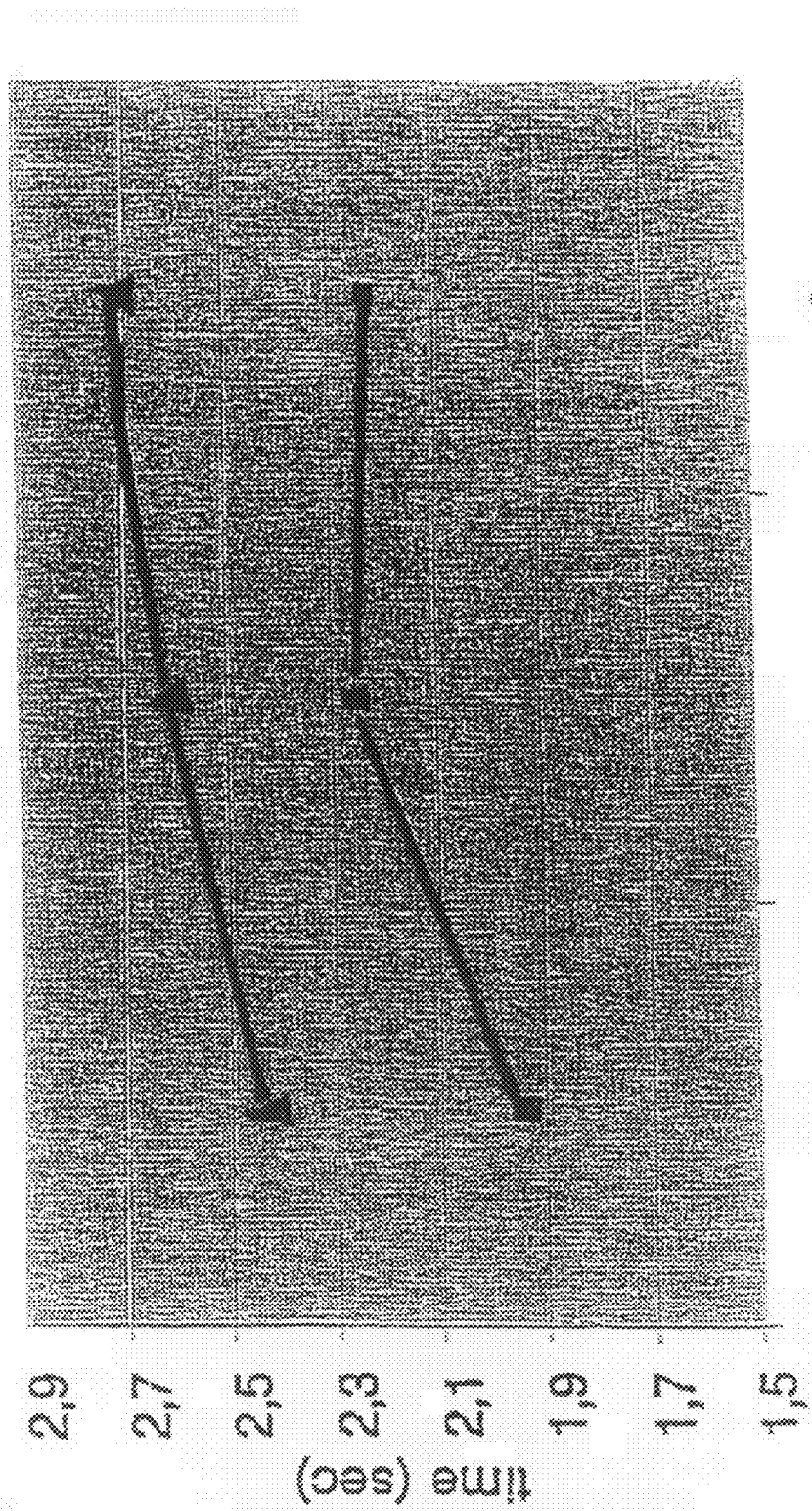
FIG. 4 shows the somatic discomfort relieving effect for ovariectomised rats given intravaginal treatments with oxytocin compared to controls receiving saline.

Besides increased motor activity, oxytocin also gives rise to relief of somatic discomfort. One way of applying somatic discomfort to an organism is to subject a part of it to a high temperature. This relief effect of oxytocin was investigated in a tail-flick test. In this test, the tails of ovariectomised rats were immersed in water at 51° C. With reference to FIG. 4, the latency time from the immersion of the tails to the withdrawal thereof were measured for rats treated with oxytocin (▲) and rats treated with saline (□). For each group of rats, the test sessions were accomplished three times with a period of 15 minutes between the sessions. As seen from FIG. 4, an intravaginal administration of oxytocin increases the latency time. A longer latency time means that the rat could stand the somatic discomfort better such as increased temperature than it otherwise would do.

Example 4

Effects of Subcutaneous Treatment with Oxytocin on Hot Flushes in Rats

In this study, ovariectomised rats (300-350 g) were treated with oxytocin for 8 days subcutaneously. Rats were addicted to morphine by implanting a morphine pellet (75 mg each) subcutaneously on days 3 and 5 of treatment. On the last day of treatment, an infrared thermistor was placed above the tail of each animal and morphine addiction was withdrawn by naloxone injection (1.0 mg/kg, subcutaneously). Temperature measurements were taken for 1 h under ketamine (80 mg/kg, intramuscularly) anaesthesia. In general, vehicle treated rats showed a 5-6° C. elevation of their tail skin temperature with the peak occurring about 15 min after naloxone injection. Repeated oxytocin treatment 1.0 mg/kg subcutaneous oxytocin or 0.1 mg/kg subcutaneous 17-alpha-ethinyloestradiol (EA) significantly inhibited the temperature increase (flushes).

Example 5

Effects of Oxytocin on Ovarian Morphology in Rats with Experimentally-Induced Polycystic Ovaries Introduction The pathogenesis of polycystic ovary syndrome (PCOS) has been attributed to dysfunction in oestrogen synthesis and/or oestrogen receptors in the ovaries. The experimentally induced rat PCO model produced by a single injection of oestradiol valerate (EV) has similarities to human PCOS, and both are associated with altered concentrations of oestrogen and hyperactivity in the sympathetic nervous system.

The main findings in the present study were that significantly higher concentrations of NGF were found in the ovaries and the adrenal glands in the rat PCO model than in the control rats, which were only injected with the vehicle (oil or NaCl) and that oxytocin treatments in PCO rats resulted in significantly lower concentrations of NGF in the ovaries compared to non-oxy-treated PCO rats. The results in the present study provide support for the theory that oxytocin inhibits hyperactivity in the sympathetic nervous system by compensating for the effects of oestrogen, possibly through the direct or indirect activation of oestrogen receptors including the orphanin ones.

Polycystic ovary syndrome (PCOS), one of the most common causes of anovulation in women of reproductive age, is a complex endocrine and metabolic disorder (Franks S. Polycystic ovary syndrome. *Arch Dis Child*, 1997; 77(1): 89-90).

Women with PCOS have an increased risk of endometrial cancer, hypertension, and type II diabetes, and they need some kind of long-standing treatment (Dahlgren E, Janson P O, Johansson S, Lapidus L, Lindstedt G, Tengborn L. Hemostatic and metabolic variables in women with polycystic ovary syndrome [see comments]. *Fertil Steril*, 1994; 61(3): 455-460). Traditional pharmacological treatment, including oestrogen, for ovulation induction is effective but side effects such as superovulation are quite common.

All rats (totally 59) received a single intramuscular injection either of oestradiol valerate (EV), oil, or 0.15 M NaCl (Kabi Pharmacia A B, Sweden) and were anaesthetised with enflurane. Twenty rats were injected with 4 mg EV in 0.2 ml oil/rat (ten rats in the control group and ten in the oxytocin treated). They were decapitated after 30 days to elucidate when the ovaries display characteristic features of well-defined PCO (Brawer et al., 1978, supra; Brawer et al., 1986, supra). The oxytocin treated group received subcutaneous oxytocin 1.0 mg/kg subcutaneously every third day during the experimental period.

Ovarian Morphology

The ovaries in the EV control group (4 mg EV in 0.2 ml oil/rat), displayed the characteristic features of well-defined PCO in rats. The ovaries in the oxytocin treated group showed significantly less changes.

The findings of the present study show that oxytocin treatment reduces the hormonal changes seen in experimentally-induced PCO.

Example 6

Effects of Oxytocin on Bone Loss

Introduction

There is a close relationship between bone mass and age in women. Osteoporosis related decrease in bone mass occurs after the age of 40 years. The rate of bone loss is accelerated in the decade, which follows the menopause. Interestingly, there is also a relationship between age and fracture rate. The fracture rate, initially low, increases rapidly in women over the age of 65 years. Also, there is a relationship between bone mass and fracture rate suggesting that the bone which is lost during the initial phases of aging is not essential to the integrity of the skeleton. Nevertheless, the decreases in bone mass with age in women would be expected to result in corresponding increases in mechanical strain on the remaining bone.

Osteoclasts are large multinuclear cells associated with the absorption and removal of bone and are, accordingly, implicated in bone loss. An object of the invention is, therefore, to counteract the action of osteoclasts. As shown in the present Example, administration of oxytocin suppresses bone loss in rats and, hence, counteracts the action of osteoclasts.

Experimental Procedure

Densitometric and Morphometric Studies. After 30 days, all rats were anesthetized and killed by exsanguination from the abdominal aorta after being anesthetized with 4 mg/100 g body weight of sodium pentothal. The femur and 5th lumbar vertebra of each rat were dissected and placed in an 85° C. water bath to remove soft tissue. Femoral length and vertebral height were measured with a caliper and bones were weighed on a precision balance. The BMC and BMD of the whole right femur and 5th lumbar vertebra were measured using a densitometer equipped with a special program for studying small animals and samples. The instrument was calibrated daily. Because of the influence of weight on bone mass in rats [Rico H, Amo C, Revilla M, Arribas I, Gonzalez-Riola J, Villa L F, Rodriguez-Puyol M Etidronate versus Clodronate in the prevention of postovariectomy bone loss. An experimental study in rats. *Clin Exp Rheumatol* 1994, 12:301-304] and human beings [Rico H, Revilla M, Villa L F, Alvarez de Buergo M A, Ruiz-Contreras D Determinants of total and regional bone mineral content and density in postpubertal normal women. *Metabolism* 1994, 43:263-266], BMC was corrected for final body weight (BMC/BW). The BMC and BMD of the femurs and 5th lumbar vertebra were measured separately.

Results

The values obtained for each parameter in every group of rats are shown in Table II. In Table II:

F-BMC means femur bone mineral content,
F-BMD means femur bone mineral density,
V-BMC means 5$^{th}$ lumbar vertebral bone mineral content,
V-BMD means 5$^{th}$ lumbar vertebral bone mineral density,
OVX means ovariectomized rats, and
OVX+Oxy means oxytocin-treated ovariectomized rats.

TABLE II

Values for each parameter in three groups of rats

|  | Controls | OVX | OVX + Oxy |
|---|---|---|---|
| Initial weight (g) | 269 ± 31 | 282 ± 27 | 277 ± 32 |
| Final weight (g) | 312 ± 22 | 331 ± 25 | 334 ± 31 |
| Femur (mm) | 34.6 ± 0.5 | 32.8 ± 1.4 | 35.5 ± 1.3 |
| Femur (mg) | 729 ± 54 | 669 ± 74 | 712 ± 42 |
| F-BMC (mg) | 399 ± 36 | 282 ± 42 | 335 ± 37 |
| F-BMD (mg/cm$^2$) | 145 ± 16 | 117 ± 17 | 131 ± 18 |
| F-BMC/BW (mg/g) | 1.38 ± 0.05 | 0.93 ± 0.08 | 1.12 ± 0.09 |
| Vertebra (mm) | 7.2 ± 0.4 | 6.4 ± 0.9 | 6.9 ± 0.6 |
| Vertebra (mg) | 269 ± 19 | 215 ± 36 | 273 ± 32 |
| V-BMC (mg) | 126 ± 17 | 88 ± 22 | 110 ± 16 |
| V-BMD (mg/cm$^2$) | 121 ± 14 | 104 ± 11 | 107 ± 13 |

Statistical analyses (P<0.05) using ANOVA shows that there were no differences in the initial body weight, and the final body weight was significantly greater in the OVX versus controls (P<0.05). Femur length did not differ significantly but femur weight was significantly lower in the OVX versus controls (P<0.05) and in OVX versus OVX–oxy (P<0.05). Femoral BMC was significantly lower in the OVX group than in the other groups (all P<0.05), and femoral BMD was significantly lower in the OVX than in the other groups (all P<0.05). Femoral BMC/BW differed in all the groups (all P<0.05). The fifth lumbar vertebra length did not differ between groups. Vertebral weight was less in the OVX group than in the other groups (all P<0.05).

Conclusion

It seems that oxytocin treatment for 10 days suppresses bone loss in ovariectomized rats.

The invention claimed is:

1. A method for treating a subject with vaginal dry membranes, said method comprising topically or parenterally administering a composition with an effective amount of a substance having oxytocin activity to said subject in need thereof, wherein the substance has an amino acid sequence selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and

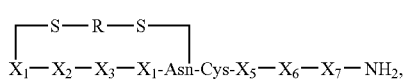

(SEQ ID NO: 2)

wherein
$X_1$ is selected from the group consisting of Cys and nothing,
$X_2$ is selected from the group consisting of Tyr, Phe, and nothing,
$X_3$ is selected from the group consisting of Ile, Val, Hoph, Phe, Cha, and nothing,
$X_4$ is selected from the group consisting of Gln, Ser, Thr, Cit, Arg, and Daba,
$X_5$ is selected from the group consisting of Pro, and nothing,
$X_6$ is selected from the group consisting of Ile, Leu, nothing, Val, Hos, Daba, Thr, and Cit,
$X_7$ is selected from the group consisting of Gly, nothing, and Ala, and
R is a chemical bond or, when $X_1$ does not represent Cys, represents nothing.

2. The method according to claim 1, wherein said composition further comprises substances that increase the release of oxytocin and/or the number or affinity of oxytocin receptors or drugs having an $\alpha_2$-agonistic effect.

3. The method according to claim 1, wherein the composition further comprises at least one pharmaceutically acceptable carrier or excipient.

4. The method according to claim 1, wherein said composition is in a form selected from the group consisting of suspension, ointment, gel, and solution.

5. The method according to claim 1, wherein the substance has the amino acid sequence of SEQ ID NO: 1.

6. The method according to claim 1, wherein the substance has the amino acid sequence of SEQ ID NO: 3.

7. The method according to claim 1, wherein the substance has the amino acid sequence of SEQ ID NO: 4.

8. The method according to claim 1, wherein the substance has the amino acid sequence of SEQ ID NO: 5.

9. The method according to claim 1, wherein the substance has the amino acid sequence of SEQ ID NO: 6.

10. The method according to claim 1, wherein the substance has the amino acid sequence of SEQ ID NO: 7.

11. The method according to claim 1, wherein the substance has the amino acid sequence of SEQ ID NO: 8.

12. The method according to claim 1, wherein the substance has the amino acid sequence of SEQ ID NO: 9.

13. The method according to claim 1, wherein the substance has the amino acid sequence of SEQ ID NO: 10.

14. The method according to claim 1, wherein the substance has the amino acid sequence of SEQ ID NO: 11.

15. The method according to claim 1, wherein the substance has the amino acid sequence of SEQ ID NO: 12.

16. The method according to claim 1, wherein the substance has the amino acid sequence of SEQ ID NO: 14.

17. The method according to claim 1, wherein the substance has the amino acid sequence of SEQ ID NO: 15.

18. The method according to claim 1, wherein the substance has the amino acid sequence of SEQ ID NO: 16.

19. The method according to claim 1, wherein the substance has the amino acid sequence of SEQ ID NO: 17.

20. The method according to claim 1, wherein the substance has the amino acid sequence of SEQ ID NO: 18.

21. The method according to claim 1, wherein the substance has the amino acid sequence of SEQ ID NO: 19.

22. The method according to claim 1, wherein the substance has the amino acid sequence of SEQ ID NO: 13.

23. The method according to claim 5, wherein said composition further comprises substances that increase the release of oxytocin and/or the number or affinity of oxytocin receptors or drugs having a $\alpha_2$-agonistic effect.

24. The method according to claim 5, wherein the composition further comprises at least one pharmaceutically acceptable carrier or excipient.

25. The method according to claim 5, wherein said composition is in a form selected from the group consisting of suspension, ointment, gel, and solution.

26. The method according to claim 5, wherein said composition is in a form selected from the group consisting of suspension, ointment, gel, and solution, and
wherein said composition further comprises substances that increase the release of oxytocin and/or the number or affinity of oxytocin receptors or drugs having an $\alpha_2$-agonistic effect.

27. The method according to claim 5, wherein the composition further comprises at least one pharmaceutically acceptable carrier or excipient.

* * * * *

UNITED STATES PATENT AND TRADEMARK OFFICE
CERTIFICATE OF CORRECTION

PATENT NO. : 7,727,959 B2
APPLICATION NO. : 11/345218
DATED : June 1, 2010
INVENTOR(S) : Kertsin Uvnäs-Moberg et al.

It is certified that error appears in the above-identified patent and that said Letters Patent is hereby corrected as shown below:

In column 27, Claim 11, delete:

" 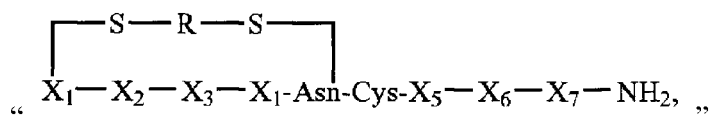 , "

and insert:

-- 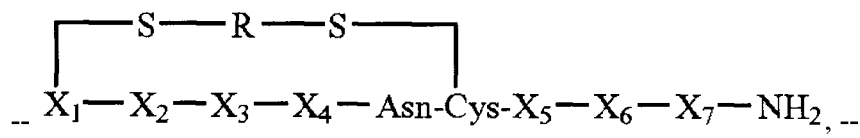 , --

Signed and Sealed this
Twenty-first Day of February, 2012

David J. Kappos
*Director of the United States Patent and Trademark Office*

SEQUENCE LISTING

```
<160> NUMBER OF SEQ ID NOS: 19

<210> SEQ ID NO 1
<211> LENGTH: 9
<212> TYPE: PRT
<213> ORGANISM: Artificial Sequence
<220> FEATURE:
<221> NAME/KEY: DISULFID
<222> LOCATION: (1)..(6)
<220> FEATURE:
<223> OTHER INFORMATION: C-term amidated
<220> FEATURE:
<223> OTHER INFORMATION: Description of Artificial Sequence: Synthetic
      peptide

<400> SEQUENCE: 1

Cys Tyr Ile Gln Asn Cys Pro Leu Gly
 1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<221> NAME/KEY: MOD_RES
<222> LOCATION: (1)
<223> OTHER INFORMATION: Cys or not present
<220> FEATURE:
<221> NAME/KEY: MOD_RES
<222> LOCATION: (2)
```

```
<223> OTHER INFORMATION: Tyr, Phe or not present
<220> FEATURE:
<221> NAME/KEY: MOD_RES
<222> LOCATION: (3)
<223> OTHER INFORMATION: Ile, Val, Hoph, Phe, Cha or not present
<220> FEATURE:
<221> NAME/KEY: MOD_RES
<222> LOCATION: (4)
<223> OTHER INFORMATION: Gln, Ser, Thr, Cit, Arg or Daba
<220> FEATURE:
<221> NAME/KEY: MOD_RES
<222> LOCATION: (7)
<223> OTHER INFORMATION: Pro or not present
<220> FEATURE:
<221> NAME/KEY: MOD_RES
<222> LOCATION: (8)
<223> OTHER INFORMATION: Ile, Leu, Val, Hos, Daba, Thr, Cit or not
      present
<220> FEATURE:
<221> NAME/KEY: MOD_RES
<222> LOCATION: (9)
<223> OTHER INFORMATION: Gly, Ala or not present
<220> FEATURE:
<223> OTHER INFORMATION: C-term amidated

<400> SEQUENCE: 2

Xaa Xaa Xaa Xaa Asn Cys Xaa Xaa Xaa
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: C-term amidated

<400> SEQUENCE: 3

Cys Tyr Ile Gln Asn Cys Pro Ile Gly
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: C-term amidated

<400> SEQUENCE: 4

Cys Tyr Ile Ser Asn Cys Pro Ile Gly
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
```

```
<220> FEATURE:
<223> OTHER INFORMATION: C-term amidated

<400> SEQUENCE: 5

Cys Phe Val Arg Asn Cys Pro Thr Gly
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: C-term amidated

<400> SEQUENCE: 6

Cys Tyr Ile Gln Asn Cys
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: C-term amidated

<400> SEQUENCE: 7

Cys Tyr Ile Gln Asn Cys Pro
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: C-term amidated

<400> SEQUENCE: 8

Cys Tyr Ile Gln Asn Cys Pro Leu
 1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 9

Tyr Ile Gln Asn Cys Pro Leu Gly
```

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 10

Ile Gln Asn Cys Pro Leu Gly
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 11

Gln Asn Cys Pro Leu Gly
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 12

Ile Gln Asn Cys Pro
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: C-term amidated

<400> SEQUENCE: 13

Cys Tyr Val Thr Asn Cys Pro Leu Gly
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID

```
<222> LOCATION: (1)..(6)
<220> FEATURE:
<221> NAME/KEY: MOD_RES
<222> LOCATION: (3)
<223> OTHER INFORMATION: Hoph
<220> FEATURE:
<223> OTHER INFORMATION: C-term amidated

<400> SEQUENCE: 14

Cys Tyr Xaa Thr Asn Cys Pro Val Gly
  1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<221> NAME/KEY: MOD_RES
<222> LOCATION: (4)
<223> OTHER INFORMATION: Cit
<220> FEATURE:
<223> OTHER INFORMATION: C-term amidated

<400> SEQUENCE: 15

Cys Tyr Phe Xaa Asn Cys Pro Leu Gly
  1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<221> NAME/KEY: MOD_RES
<222> LOCATION: (3)
<223> OTHER INFORMATION: Cha
<220> FEATURE:
<221> NAME/KEY: MOD_RES
<222> LOCATION: (8)
<223> OTHER INFORMATION: Hos
<220> FEATURE:
<223> OTHER INFORMATION: C-term amidated

<400> SEQUENCE: 16

Cys Tyr Xaa Arg Asn Cys Pro Xaa Ala
  1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: DISULFID
<222> LOCATION: (1)..(6)
<220> FEATURE:
<221> NAME/KEY: MOD_RES
<222> LOCATION: (4)
<223> OTHER INFORMATION: Daba
<220> FEATURE:
<221> NAME/KEY: MOD_RES
<222> LOCATION: (8)
<223> OTHER INFORMATION: Daba
<220> FEATURE:
<223> OTHER INFORMATION: C-term amidated

<400> SEQUENCE: 17

Cys Tyr Val Xaa Asn Cys Pro Xaa Ala
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<221> NAME/KEY: MOD_RES
<222> LOCATION: (3)
<223> OTHER INFORMATION: Hoph
<220> FEATURE:
<221> NAME/KEY: MOD_RES
<222> LOCATION: (4)
<223> OTHER INFORMATION: Daba
<220> FEATURE:
<221> NAME/KEY: MOD_RES
<222> LOCATION: (8)
<223> OTHER INFORMATION: Cit
<220> FEATURE:
<223> OTHER INFORMATION: C-term amidated

<400> SEQUENCE: 18

Cys Tyr Xaa Xaa Asn Cys Pro Xaa Ala
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: C-term amidated

<400> SEQUENCE: 19

Cys Tyr Phe Arg Asn Cys Pro Val Ala
 1               5
```